US006475755B2

(12) United States Patent
Ciliberto et al.

(10) Patent No.: US 6,475,755 B2
(45) Date of Patent: Nov. 5, 2002

(54) ADENOVIRAL VECTORS FOR MUTANTS OF HUMAN INTERLEUKIN 6 (HIL-6) WITH HIL-6 ANTAGONIST ACTIVITY, PHARMACEUTICAL COMPOSITIONS THEREWITH AND THEIR USES

(75) Inventors: Gennaro Ciliberto; Isabella Saggio, both of Rome; Rocco Savino, Pomerzia RM, all of (IT); Michel Perricaudet, Ecrosnes (FR)

(73) Assignees: Instituto di Ricerche di Biologgia Molecolare, Rome (IT); Centre National de la Recherche Scientifique, Paris Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,948
(22) PCT Filed: Sep. 24, 1997
(86) PCT No.: PCT/IT97/00231
§ 371 (c)(1),
(2), (4) Date: Jun. 30, 1999
(87) PCT Pub. No.: WO98/13383
PCT Pub. Date: Apr. 2, 1998

(65) Prior Publication Data
US 2002/0012656 A1 Jan. 31, 2002

(30) Foreign Application Priority Data
Sep. 24, 1996 (IT) ......................... RM96A0650

(51) Int. Cl.$^7$ .......................... C12P 21/06; C12P 21/02; C12P 21/04; C12N 15/06; C12N 15/00
(52) U.S. Cl. .................. 435/69.52; 435/69.1; 435/69.5; 435/320.1
(58) Field of Search ...................... 424/93.2; 435/320.1, 435/69.1, 69.52, 456; 514/44; 530/351; 536/23.1, 23.5, 24.1

(56) References Cited

FOREIGN PATENT DOCUMENTS

WO    WO 96/18648    6/1995
WO    WO 95/2409    10/1995

OTHER PUBLICATIONS

Saggio et al., Adenovirus–mediated gene transfer of a human IL–6 antagonist, Gene Ther., 4:839–845, Aug. 1997.*

Sporeno et al., Human interleukin–6 receptor super–antagonists with high potency and wide spectrum on multiple myeloma cells, Blood, 87(11):4510–4519, Jul. 1996.*

Levrero et al., Defective and nondefective adenovirus vectors for expressing foreign genes in vitro and in vivo, Gene, 101:195–202, May 1991.*

Mastrangeli et al., Diversity of airway epithelial cell targets for in vivo recombinant adenovirus–mediated gene transfer, J. Clin. Invest., 91:225–234, Jan. 1993.*

McElvaney and Crystal, IL–6 release and airway administration of human CFTR cDNA adenovirus vector, Nat. Med., 1(3):182–184, Mar. 1995.*

Anderson, Human gene therapy, Nature, 392 (Supp):25–30, Apr. 1998.*

Verma and Somia, Nature, 389:239–242, Sep. 1997.*

Niiler; FDA, researchers consider first transgenic fish 2000, Nature Biotechnology, vol. 18: 143.*

Saggio I. et al., "Adenovirus–mediated gene transfer of a human IL–6 antagonist.", Gene Therapy, vol. 4, No. 8, Aug. 1997, pp. 839–845.

Savino, R. et al., "Generation of interleukin–6 receptor antagonists by molecular–modeling guided mutagenesis of residues important for GP130 activation.", EMBO Journal, vol. 13, No. 6, Mar. 15, 1994, pp. 1357–1367.

Hon De F.D. et al., "Leucine–58 in the putative 5th helical region of human interleukin (IL)–6 is important for activation of the IL–6 siganl transducer, GP130.", FEBS Letters, vol. 369, 1995, pp. 187–191.

Ehlers, M. et al., "Combining two mutations of human interleukin–6 that affect GP130 activation results in a potent interleukin–6 receptor antagonist on human myeloma cells.", Journal of Biological Chemistry, vol. 270, No. 14, Apr. 7, 1995, pp. 8158–8163..

Savino, R. et al., "Rational design of a receptor super–antagonist of human interleukin–6.", EMBO Journal, vol. 13, No. 24, 1994, pp. 5863–5870.

* cited by examiner

Primary Examiner—Deborah Crouch
Assistant Examiner—Joseph Woitach
(74) Attorney, Agent, or Firm—Anna L. Cocuzzo; Jack L. Tribble

(57) ABSTRACT

The subject matter of the present invention are recombinant defective adenoviruses comprising a heterologous DNA sequence coding for a mutein having the activity of human Interleukin 6 (hIL-6) antagonists or superantagonist. Moreover, the invention refers to therapeutical uses thereof, in particular for preparing pharmaceutical compositions for treating and/or preventing pathologies caused by hIL-6 overproduction.

8 Claims, No Drawings

ADENOVIRAL VECTORS FOR MUTANTS OF HUMAN INTERLEUKIN 6 (HIL-6) WITH HIL-6 ANTAGONIST ACTIVITY, PHARMACEUTICAL COMPOSITIONS THEREWITH AND THEIR USES

DESCRIPTION

The present invention refers to recombinant defective adenoviruses containing a DNA sequence coding for hIL-6 (human Interleukin 6) antagonists and/or superantagonists. Such recombinant adenoviruses are used for the preparation of pharmaceutical compositions, in particular in gene therapy for the treatment and/or prevention of diseases caused by hIL-6 overproduction.

Altered hIL-6 serum levels have been described in several pathologies, such as multiple myeloma (1), Castleman's disease (2), mesangial glomerulonephritis (3), osteoporosis (4), EBV positive lymphomas (5), rheumatoid arthritis (6) and systemic lupus erythematosus (7). In multiple myeloma, IL-6 clearly plays an autocrine and paracrine role in the growth of malignant cells.

It is known from WO 95/26409 and WO 95/25508, in the name of Rhone-Poulenc Rorer S.A., the use of recombinant defective adenoviruses to achieve stable expression of a protein of interest (in particular a cytokine as in the case of WO 95/26409), whose coding sequence is inserted in the defective adenovirus genome under the control of a strong promoter. It is also known that, in the case of adenovirus mediated gene therapy, inflammation represents a major obstacle, being the cause for tissue injury as well as, at least in part, for termination of gene expression (9) (10). There are indications that IL-6 is the major inflammatory cytokine produced after adenovirus injection (11) (12).

Now, it has been unexpectedly found that mutants of hIL-6 with antagonist or superantagonist activity over hIL-6 (disclosed in WO/00852 in the name of the present Applicant) produced by cells infected both in vitro and in vivo with a recombinant defective adenovirus, containing a DNA sequence coding for said antagonists or superantagonists under the control of a strong promoter, inhibit hIL-6 activity on a variety of human cells. Therefore, said recombinant adenoviruses can be used to prolong adenovirus mediated gene of interest expression in vivo.

The subject matter of the present invention is a recombinant defective adenovirus comprising a DNA or a cDNA sequence coding for a mutant of human Interleukin 6, a fragment thereof or a derivative thereof, with antagonist or superantagonist activity over hIL-6.

In preferred embodiments of the invention, the hIL-6 mutants with superantagonist activity over hIL-6 are Tyr31Asp, Gly35Phe, Ser118Arg, Val121Asp, Gln175Ile, Ser176Arg, Gln183Ala and Tyr31Asp, Gly35Phe, Leu57Asp, Glu59Phe, Asn60Trp, Gln75Tyr, Ser76Lys, Ser118Arg, Val121Asp, Gln175Ile, Ser176Arg, Gln183Ala (hereinafter referred to also as Sant1 and Sant7 respectively).

The recombinant defective adenovirus of the invention can be put under the control of signals allowing its expression in different kinds of human specific cells. The expression signals can be selected among the viral promoters. The viral promoter can be Rous Sarcoma Virus (RSV).

The invention also refers to the use of the recombinant defective adenovirus, comprising at least a DNA or a cDNA sequence coding for a mutant of hIL-6, a fragment thereof or a derivative thereof, with antagonist or superantagonist activity over hIL-6, for treating and/or preventing diseases such as multiple myeloma, Castleman's disease, mesangial glomerulonephritis, osteoporosis, EBV positive lymphomas, rheumatoid arthritis and systemic lupus erythematosus.

Pharmaceutical compositions comprising at least one of the above recombinant defective adenoviruses are also the subject matter of the present invention. The pharmaceutical compositions can be in injectable form. They can contain the recombinant defective adenovirus in the range from $10^4$ to $10^{14}$ pfu/ml (plaque forming unit/ml), preferably from $10^6$ to $10^{10}$ pfu/ml. Mammalian cells, in particular human cells, infected by at least one of the above recombinant adenoviruses are a further subject of the present invention. These cells can additionally express a gene of interest coding for a therapeutic protein. These cells can be further infected with at least one virus expressing a therapeutic gene.

The infected human cells can be selected from the group comprising fibroblasts, myoblasts, hepatocytes, endothelial cells, glial cells and keratinocytes.

Another subject matter of the present invention is an implant comprising the cells infected by at least one of the above recombinant defective adenoviruses and an extracellular matrix. The extracellular matrix can be a gelifying compound which can be selected from the group consisting of collagen, gelatin, glucosaminoglycans, fibronectins and lectins. The extracellular matrix can comprise a support for anchoring the infected cells. The support can be preferably made of polytetrafluoroethylene fibers.

The objects, characteristics and advantages of the invention will be further illustrated, although not limited, by the following examples directed to embodiments thereof.

EXAMPLE 1

Construction of a Recombinant Adenovirus, Called AdRSVhIL-6α, Containing the Sequence Coding for the Mutant IL-6 Form Called Sant1 and Characterised by Having the Mutations Tyr31Asp, Gly35Phe, Ser118Arg, Val121Asp, Gln175Ile, Ser176Arg and Gln183Ala For the construction of AdRSVhIL-6α, the cDNA coding for Sant1 (described in WO95/00852 by the same applicant and characterized by having the seven amino acid substitutions Tyr31Asp, Gly35Phe, Ser118Arg, Val121Asp, Gln175Ile, Ser176Arg and Gln183Ala as compared with wt hIL-6) was subcloned together with hIL-6 leader sequence in the adenoviral vector pAdRSVβgal (20), cleaved with the restriction enzymes SalI and EcoRV. The recombinant plasmid was cotransfected together with ClaI restricted AdRSVβgal genome (20) into human embryonic kidney 293 cells (ECACC). Recombinant plaques were isolated and amplified as described in (14) (15). DNA pattern of recombinant AdRSVhIL-6α ( was controled by multiple restriction analysis.

All viral stocks were prepared in 293 cells and purified twice on isopicnic CsCl gradient. Desalting was performed using Pharmacia G50 columns. Viruses were aliquoted and kept in PES-15% glycerol at −80° C. Titers, calculated by plaque analysis on 293 cells, varied from 1 to $2 \times 10^{11}$ pfu/ml.

EXAMPLE 2

Cells Infected in vitro with the Recombinant Adenovirus AdRSVhIL-6α. Produce Sant1 in the Cell Culture Supernatant To test antagonist expression by the AdRSVhIL-6α, constructed as described in the above example, 35 mm falcon plates of subconfluent human embryonic kidney 293 cells were infected in 3 ml of medium with 10 plaque forming units (pfu)/cell of a purified AdRSVhIL-6α ( stock, prepared as described in the example 1. 24 hours after infection, supernatants were collected and concentrated 5-fold with centricon 3 tubes (Amicon). 25 μl of concentrated supernatants were loaded on acrylamide gel. The gel was electroblotted and nitrocellulose membrane was blocked overnight in TBS-5% milk-0.05% Tween 20. After washing in TBS-0.05% Tween 20, the membrane was incubated two hours with polyclonal anti-hIL6 antibodies (R&D, hIL6 ELISA kit), coupled to horse-radish peroxidase, diluted 1:2, v/v, in TBS-5% milk-0.05% Tween 20. After washing with TBS-0.05% Tween 20, the membrane was revealed with ECL bioluminescence kit (Amersham) following the instructions furnished by the manufacturer. A single band, of the expected molecular mass, was detected in the supernatants of cells infected with AdRSVhIL-6α, but not in the supernatants of cells infected with AdRSVβgal, or in the supernatants of mock-infected cells. Therefore cells infected with AdRSVhIL-6α ( express and secrete in the cell culture supernatant a protein of the same size as hIL-6 and as Sant1 (which is a mutant form of hIL-6 itself) and which is recognised by antibodies raised against hIL-6.

EXAMPLE 3

Sant1 Expressed in vitro by Cells Infected with AdRSVhIL-6α ( Inhibits hIL-6 Biological Activity on Human Hepatoma Cells It is well known in the state of the art that IL-6 stimulates the transcription of a set of genes (known as Acute Phase Genes) in liver cells or in liver-derived hepatoma cell lines in culture. In particular, IL-6 stimulates the transcription by the C-reactive gene promoter in human Hep3B hepatoma cells ((13), and references therein).

To test whether the Sant1 produced by the recombinant virus was able to inhibit the IL-6 biological activity described above, 35 mm falcon plates of subconfluent human embryonic kidney 293 cells were infected with AdRSVhIL-6α ( or AdRSVβgal (in 3 ml of medium with 10 plaque forming unit (pfu)/cell of a purified stock), 24 hours after infection supernatants were collected and tested for inhibition of hIL-6 biological activity on human Hep3B hepatoma cells. The effectiveness of transcriptional stimulation was measured according to the state of the art (13). Human Hep3B hepatoma cells were stimulated with 4 ng/ml of hIL-6, and this extent of stimulation was taken as 100%, or with 4 ng/ml of hIL-6 in the presence of serial dilutions of cell culture supernatant obtained from AdRSVhIL-6α ( infected 293 cells; in the latter cases the extent of transcriptional stimulation was expressed as percent of the stimulation obtained in cells incubated with 4 ng/ml of hIL-6 only. The results of the experiment are given in Table 1 below.

TABLE 1

Inhibition of hIL-6 biological activity on human Hep3B hepatoma cells by serial dilutions of cell culture supernatant obtained from AdRSVhIL-60 infected 293 cells.

| Serum dilution | Biological activity (% of the control) |
| --- | --- |
| 1:2916 | 85.8% |
| 1:972 | 87.7% |
| 1:324 | 72.3% |
| 1:108 | 57.0% |
| 1:36 | 28.1% |
| 1:12 | 23.8% |
| 1:4 | 8.1% |

It can be seen that the cell culture supernatant obtained from AdRSVhIL-6α ( infected 293 cells diluted 1:4 inhibit completely the bioactivity of 4 ng/ml of hIL-6 on human Hep3B hepatoma cells. Inhibition was not due to toxicity, because in the presence of molar excess of hIL-6 (1000 ng/ml) the C-reactive protein gene promoter activity was rescued up to 100% (data not shown). The data reported in table 1 above can be used to plot a dose-inhibition curve, from which it can be interpolated that 50% of inhibition of IL-6 activity is obtained at a serum dilution of 1:60. In a parallel inhibition experiment performed not with AdRSVhIL-6α ( infected 293 cells supernatant, but with recombinant, E. coli produced Sant1, 50% of inhibition of IL-6 activity is obtained at a protein concentration of 10 ng/ml. Therefore, the Sant1 concentration in undiluted AdRSVhIL-6α ( infected 293 cells supernatant can be calculated multiplying the concentration of Sant1 needed to reach 50% inhibition of IL-6 activity on Hep3B hepatoma cells (10 ng/ml) times the AdRSVhIL-6α ( infected 293 cells supernatant dilution factor (60) which gives 50% inhibition of IL-6 activity. The calculation gives:

Sant1 concentration in undiluted AdRSVhIL-6α ( infected 293 cells supernatant=

=10 ng/ml×60=600 ng/ml.

EXAMPLE 4

Sant1 Expressed in vitro by Cells Infected with AdRSVhIL-6α ( Inhibits hIL-6 Biological Activity on Human Myeloma Cells In the previous example it was shown that the cell culture supernatant obtained from AdRSVhIL-6α ( infected 293 cells was able to inhibit interleukin 6 biological activity (stimulation of transcription by an IL-6 inducible promoter) on human hepatoma cells. In the introductory part of the above description it is stated that altered IL-6 serum levels have been described in several pathologies, like various forms of multiple myeloma/plasmacytoma. We provide here a further example by showing that the cell culture supernatant obtained from AdRSVhIL-6α ( infected 293 cells fully inhibit the interleukin 6-dependent growth of a human myeloma cell line, called XG-1, derived from freshly isolated myeloma cells obtained from a patient with terminal disease. The XG-1 myeloma cell line growth is strictly dependent on exogenously added IL-6, similarly to what has been shown for fresh myeloma cells, therefore this cell line can be considered an excellent in vitro model of the multiple myeloma (16).

To test mutants antagonism on wild type interleukin 6, XG-1 myeloma cells were cultured in 96-well microtiter plates at 6000 cell/microwell with hIL-6 at 0.1 nanograms per milliliter (ng/ml) of culture medium, in the presence of serial dilutions of cell culture supernatant obtained from AdRSVhIL-6α infected 293 cells as described in the previous example. After 7 days of culture, cell numbers were evaluated by colorimetric determination of hexosaminidase levels (17). The following Table 2 shows the inhibition of hIL-6 activity as a function of the dilutions of cell culture supernatant obtained from AdRSVhIL-6α infected 293 cells.

TABLE 2

Inhibition of hIL-6 biological activity on human XG-1
myeloma cells by serial dilutions of cell culture
supernatant obtained from AdRSVhIL-6α infected 293 cells.

| Serum dilution | Biological activity (% of the control) |
| --- | --- |
| 1:2916 | 84.7% |
| 1:972 | 83.1% |
| 1:324 | 80.5% |
| 1:108 | 61.0% |
| 1:36 | 46.1% |
| 1:12 | 28.2% |
| 1:4 | 7.0% |

It can be seen that the cell culture supernatant obtained from AdRSVhIL-6α infected 293 cells diluted 1:4 inhibit completely the growth stimulatory effect of 0.1 ng/ml of hIL-6 on human XG-1 myeloma cells. As it was in the previous example, inhibition was not due to toxicity, because in the presence of molar excess of hIL-6 (100 ng/ml) XG-1 cell growth was rescued up to 100% (not shown). The data reported in table 2 above can be used to plot a dose-inhibition curve, from which it can be interpolated that 50% of inhibition of IL-6 activity is obtained at a serum dilution of 1:40. In a parallel inhibition experiment performed not with AdRSVhIL-6α infected 293 cells supernatant, but with recombinant, E. coli produced Sant1, 50% of inhibition of IL-6 activity is obtained at a protein concentration of 20 ng/ml. Therefore, the Sant1 concentration in undiluted AdRSVhIL-6α infected 293 cells supernatant can be calculated multiplying the concentration of Sant1 needed to reach 50% inhibition of IL-6 activity on XG-1 myeloma cells (20 ng/ml) times the AdRSVhIL-6α infected 293 cells supernatant dilution factor (40) which gives 50% inhibition of IL-6 activity. The caculation gives:

Sant1 concentration in undiluted AdRSVhIL-6α infected 293 cells supernatant=

=20 ng/ml×40=800 ng/ml which is in very good agreement with the estimate of Sant1 concentration in undiluted AdRSVhIL-6α infected 293 cells supernatant obtained in the previous example (600 ng/ml).

EXAMPLE 5

Animals Infected with the Recombinant Adenovirus AdRSVhIL-6Produce Sant1

To test in vivo antagonist expression by the AdRSVhIL-6α, constructed as described in the example 1, 6 to 8 weeks old mice (purchased from IFFACREDO, France) were injected in the orbital vein with the standard dose of $2\times10^9$ pfu/mouse, diluted in 100 µl of PBS. Blood was collected at different times after the injection by puncture in the orbital vein after treating the animal with ether. Sera were prepared according to the state of the art and the antagonist concentration in the serum was measured according to the state of the art by means of a "sandwich" ELISA test, using a commercially available kit produced by the company "R&D Systems", and scrupulously following the manufacturer's instructions. The experiment demonstarted that intra-venous (iv) injection of $2\times10^9$ pfu of AdRSVhIL-6α in 6 to 8 weeks old mice allowed expression of Sant1 at a concentration of 5 ng/ml, for at least two months.

EXAMPLE 6

Sant1 Produced in vivo in Mice Infected with AdRSVhIL-6α ( Inhibits hIL-6 Induced APRF Activation in Human Myeloma Cells It is well known in the art that one of the first steps in IL-6 induced cell activation is tyrosine phosphorylation of the acute phase transcription factor (APRF). Upon phosphorylation, APRF acquires the ability to bind specific DNA sequences (acute phase response elements: APREs), and migrates to the nucleus (18).

To test whether the Sant1 produced in vivo by the recombinant adenovirus was able to inhibit the IL-6 biological activity described above, sera of mice injected with $2\times10^9$ pfu of AdRSVhIL-6α or of control adenovirus were collected at day 40 after the injection as described in the previous example, concentrated and tested on human XG-1 myeloma cells for inhibition of hIL-6 biological activity described above. After 4 hours of IL-6 deprivation, XG-1 cells were incubated for 15 minutes at 37° C. with culture medium without IL-6, with 0.2 ng/ml of IL-6 in the presence of 50% serum of uninjected mice, with 0.2 ng/ml of IL-6 in the presence of 50% serum of mice injected with AdRSVhIL-6( and with 0.2 ng/ml of IL-6 in the presence of 50% serum of mice injected with control virus. Whole cell extract were prepared and APRF activation was monitored by gel retardation as described in the art (18). APRF activation for the various samples was quantified at the phosphoimager and the extent of activation in the various samples was expressed as percent of the activation obtained in cells stimulated with 0.2 ng/ml of IL-6 in the presence of 50% serum of uninjected mice. The results of the experiment are reported in table 3 below.

TABLE 3

Inhibition of hIL-6 induced APRF activation in human XG-1
myeloma cells by serum of mice injected with AdRSVhIL-6α
or with control adenovirus

| Sample | APRF activation (% of the control) |
| --- | --- |
| no IL-6 | 0% |
| 0.2 ng/ml IL-6, 50% serum of uninjected mice | 100% |
| 0.2 ng/ml IL-6, 50% serum of AdRSVhIL-6( injected mice | 5% |
| 0.2 ng/ml IL-6, 50% serum of control adenovirus injected mice | 75% |

As shown, serum from mice injected with AdRSVhIL-6α recombinant adenovirus and containing Sant1 expressed in vivo as described in the previous example effectively inhibit APRF activation induced by 0.2 ng/ml of IL-6 in XG-1 cells. Again, inhibition was not due to toxicity, because in the presence of molar excess of hIL-6 (100 ng/ml) the IL-6 induced APRF activation was fully rescued (not shown). Moreover, table 3 also show that serum from mice injected with control recombinant adenovirus failed to inhibit significantly APRF activation induced by 0.2 ng/ml of IL-6 in XG-1 cells.

REFERENCES (1) Klein B, Brailly H. (1995) Immunol. Today 16:216-220.
(2) Brandt, S. J., Bodine, D. M., Dunbar, C. E. and Nienhuis, A. W. (1990) J. Clin. Invest. 86:592-599.
(3) Horii, Y. et al. (1989) J. Immunol. 143:3949–3955.
(4) Jilka R L, Giao H, Girasole G, Passeri G, Williams D C, Abrams J S, Boyce B, Broxmeyer H and Manolagas S C (1992) Science 257:88–91.
(5) Durandy A, Emilie D, Peuchmar M, et al. (1994) J. Immunol. 152:5361–5367.
(6) Hermann E, Fleisher B, Mayer W J, Poralla T, and Meyer Zum Beschernfelde K H (1989) Clin. Exp. Rheumatol. 7:411–414.

(7) Hirohata S, Myiamoto T. (1990) Arthritis Rheum. 33:644–649.
(8) Swaak A, van Rooyen A, Aarden L A. (1989) Rheumatol. Int 8:263–268.
(9) Engelhardt J F, Ye X, Doranz B, Wilson J. (1994) Proc. Natl. Acad. Sci. 91:6196–6200.
(10) McCoy R D, Davidson B L, Roessler B J, et al. (1995) Hum Gene Ther 6:1553–1560.
(11) Ginsberg H S, Moldawer L L, Sehgal P B, et al. (1991) Proc. Natl. Acad. Sci. 88:1651–1655.
(12) Crystal R G, McElvaney N G, Rosenfeld M A, et al. (1994) Nature Genetics 8:42–51.
(13) Gregory B, Savino R and Ciliberto G. (1994) J. Immunological Methods 170:47–56
(14) Graham F L, Van der Eb E J. (1973) Virology 52:456–467.
(15) Graham F L, Smiley J, Russel W C, Nairn R. (1977) J. Gen. Virol. 36:59–72.
(16) Jourdan M, Zhang X -G, Portier M, Boiron J -M, Bataille R and Klein B. (1991) J. Immunol. 147:4402–4407.
(17) Landegren, U. (1984) J. Immunol. Methods 67:379–388
(18) Lütticken C, Wegenka U M, Buschmann J, Schindler C, Ziemiecki A, Harpur A G, Wilks A F, Yasukawa K, Taga T, Kishimoto T, Barbieri G, Pellegrini S, Sendtner M, Heinrich P C and Horn F (1994) Science 263:89–92.
(19) Stratford-Perricaudet L D, Makeh I, Perricaudet M, Briand P. (1992) J. Clin. Invest. 90:626–630.

What is claimed is:

1. A method for inhibiting the activity of IL-6 in a population of human cells in vitro comprising introducing into said human cells a recombinant defective adenovirus, comprising DNA encoding mutant human interleukin 6 (hIL-6); said mutant hIL-6 comprising amino acid substitutions Tyr31 Asp, Gly35 Phe, Ser118Arg, Val121Asp, Gln175Ile, Ser176Arg, and Gln183Ala.

2. A method in accordance with claim 1 wherein the DNA encoding mutant hIL-6 is cDNA.

3. A method for inhibiting the activity of IL-6 in a population of human cells in vitro comprising introducing into said human cells a recombinant defective adenovirus, comprising DNA encoding mutant human interleukin 6 (hIL); said mutant hIL-6 comprising amino acid substitutions Tyr31Asp, Gly35Phe, Leu57Asp, Glu59Phe, Asn60Trp, Gln75Tyr, Ser76Lys, Ser118Arg, Val121Asp, Gln175Ile, Ser176Arg, and Gln183Ala.

4. A method in accordance with claim 3 wherein the DNA encoding the mutant hIL-6 is operatively linked to a viral promoter which promotes the expression of the mutant hIL-6 in a human cell of interest.

5. A method in accordance with claim 4 wherein the viral promoter is a Rous Sarcoma Virus (RSV) promoter.

6. A method in accordance with claim 3 wherein the DNA encoding mutant hIL-6 is cDNA.

7. A method in accordance with claim 1 wherein the DNA encoding the mutant hIL-6 is operatively linked to a viral promoter, which promotes the expression of the mutant hIL-6 in a human cell of interest.

8. A method in accordance with claim 7 wherein the viral promoter is a Rous Sarcoma Virus (RSV) promoter.

* * * * *

UNITED STATES PATENT AND TRADEMARK OFFICE
CERTIFICATE OF CORRECTION

PATENT NO.   : 6,475,755 B2
DATED        : November 5, 2002
INVENTOR(S)  : Ciliberto et al.

It is certified that error appears in the above-identified patent and that said Letters Patent is hereby corrected as shown below:

<u>Column 8,</u>
Line 4, "Tyr 31 Asp, Gly35 Phe," should read -- Tyr 31Asp, Gly35Phe, --.
Line 12, "(hIL); said" should read -- (hIL-6); said --.

Signed and Sealed this

Thirty-first Day of May, 2005

JON W. DUDAS
*Director of the United States Patent and Trademark Office*